United States Patent [19]
Stenman et al.

[11] Patent Number: 5,976,809
[45] Date of Patent: Nov. 2, 1999

[54] ASSAY OF FREE AND COMPLEXED TRYPSINOGEN-2

[75] Inventors: Ulf-Håkan Stenman, Heikelsvägen 10, Grankulla; Johan Hedström, Helsingfors, both of Finland

[73] Assignee: Ulf-Hakan Stenman, Grankulla, Finland

[21] Appl. No.: 08/793,534

[22] PCT Filed: Aug. 24, 1995

[86] PCT No.: PCT/FI95/00453

§ 371 Date: Aug. 13, 1997

§ 102(e) Date: Aug. 13, 1997

[87] PCT Pub. No.: WO96/07104

PCT Pub. Date: Mar. 7, 1996

[30] Foreign Application Priority Data

Aug. 26, 1994 [FI] Finland ..................................... 943921

[51] Int. Cl.$^6$ ........................ G01N 33/53; G01N 33/573; A61K 35/14
[52] U.S. Cl. .............................. 435/7.1; 435/7.1; 435/7.4; 435/7.92; 435/7.93; 435/7.94; 435/7.95; 436/811; 530/380
[58] Field of Search .......................... 435/7.1, 7.4, 7.92, 435/7.94, 7.95, 7.93; 436/811; 530/380

[56] References Cited

FOREIGN PATENT DOCUMENTS 0 048 989  4/1982  European Pat. Off. .
30 16 575  11/1981  Germany .

OTHER PUBLICATIONS

Vercaigne–Marko, D. (1989). "Human Cationic and Anionic Trypsins: Differences of Interaction with $\alpha_1$–Proteinase Inhibitor." *Biol. Chem. Hoppe–Seyler* 370:1163–1171.

Itkonen, O. et al. (1990). "Time–resolved immunofluorometric assays for trypsinogen–1 and 2 in serum reveal preferential elevation of trypsinogen–2 in pancreatitis." *J. Lab Clin. Med.* 115:712–718.

Koivunen, E. et al. (1990). "Cyst Fluid of Ovarian Cancer Patients Contains High Concentrations of trypsinogen–2." *Cancer Res.* 50:2375–2378.

*Chem. Abstracts* 114:243198x (1991).

*Chem. Abstracts* 115:3672z (1991).

Dialog Information Service, file 155, Medline, Dailog accession No. 05400454, Medline accession No. 85016454 Abstract of Borgstrom A. et al., *Scand. J. Clin. Lab. Invest.* 44:381–6 (1984). 1985 accession No.

Dialog Information Service, file 155, Medline, Dialog accession No. 06301754, Medline accession No. 87275754 Abstract of Fabris, C. et al., *Enzyme* 37:174–81 (1987).

National Library of Medicine, file Medline, Medline accession No. 94349572 Abstract of Hedstr:om, J. et al., *Clin. Chem.* 40:1761–5 (1994).

Guy et al., "Two Human Trypsinogens, Purification, Molecular Properties, and N–Terminal Sequences," *Biochemistry*, 17(9):1669–1675, 1978.

Hedstrom et al., "Time–Resolved Immunofluorometric Assay of Trypsin–2 Complexed with alpha–1–Antitrypsin in Serum," *Clinical Chemistry*, 40(9):1761–1765, Sep. 1994.

Hedstrom et al., "Urine trypsinogen–2 as marker of acute pancreatitis," *Clinical Chemistry*, 42(5):685–690, 1996.

Hedstrom et al., "Urinary trypsinogen–2 test strip for acute pancreatitis," *The Lancet*, 347:729–731, Mar. 16, 1996.

Kemppainen et al., "Rapid Measurement of Urinary Trypsinogen–2 as a Screening Test for Acute Pancreatitis," *The New England Journal of Medicine*, 336(25):1788–1793, Jun. 19, 1997.

Kimland et al., "Immunoreactive anionic and cationic trypsin in human serum," *Clinica Chimica Acta*, 184:31–46, 1989.

*Primary Examiner*—James C. Housel
*Assistant Examiner*—Ja-Na A. Hines
*Attorney, Agent, or Firm*—Rothwell, Figg, Ernst & Kurz, p.c.

[57] ABSTRACT

The invention relates to an immunoassay for trypsinogen-2 wherein an amount of analyte in a sample is measured, said analyte being either trypsin-2 complexed with alpha-1-antitrypsin (trypsin-2-AAT) in serum, or trypsinogen-2 in urine. According to a preferred embodiment, the trypsin-2-AAT complex or free trypsinogen-2 are measured by noncompetitive methods employing at least two different antibodies. The methods are useful for the diagnosis of patients with pancreatic disease, especially pancreatitis.

16 Claims, 9 Drawing Sheets

ASSAY OF FREE AND COMPLEXED TRYPSINOGEN-2

The present invention provides an immunoassay for the measurement of trypsinogen-2 either as free trypsinogen-2 in urine or as its complex with alpha-1-antitrypsin (trypsin-2-AAT) in serum. The invention relates further to a method for differentiating between pancreatitis and other pancreatic disease on one hand and non-pancreatic gastrointestinal disease on the other hand by determining either free trypsinogen-2 in urine or trypsin -2-AAT in serum.

BACKGROUND OF THE INVENTION

The publications and other materials used herein to illuminate the background of the invention, and in particular, cases to provide additional details respecting the practice, are incorporated by reference.

The trypsinogens are serine proteases secreted by exocrine cells of the pancreas (Travis J and Roberts R. Biochemistry 1969; 8: 2884–9; Mallory P and Travis J, Biochemistry 1973; 12: 2847–51). Two major types of trypsinogen isoenzymes have been characterized, trypsinogen-1, also called cationic trypsinogen, and trypsinogen-2 or anionic trypsinogen. The trypsinogen proenzymes are activated to trypsins in the intestine by enterokinase, which removes an activation peptide from the N-terminus of the trypsinogens. The trypsinogens show a high degree of sequence homology, but they can be separated on the basis of charge differences by using electrophoresis or ion exchange chromatography. The major form of trypsinogen in the pancreas and pancreatic juice is trypsinogen-1 (Guy CO et al., Biochem Biophys Res Commun 1984; 125: 516–23). In serum of healthy subjects, trypsinogen-1 is also the major form, whereas in patients with pancreatitis, trypsinogen-2 is more strongly elevated (Itkonen et al., J Lab Clin Med 1990; 115:712–8). Trypsinogens also occur in certain ovarian tumors, in which trypsinogen-2 is the major form (Koivunen et al., Cancer Res 1990; 50: 2375–8). Trypsin-1 in complex with alpha-1-antitrypsin, also called alpha-1-antiprotease, has been found to occur in serum of patients with pancreatitis (Borgstrom A and Ohlsson K, Scand J Clin Lab Invest 1984; 44: 381–6) but determination of this complex has not been found useful for differentiation between pancreatic and other gastrointestinal diseases (Borgstrom et al., Scand J Clin Lab Invest 1989; 49:757–62).

Trypsinogen-1 and -2 are closely related immunologically (Kimland et al., Clin Chim Acta 1989; 184: 31–46; Itkonen et al., 1990), but by using monoclonal antibodies (Itkonen et al., 1990) or by absorbing polyclonal antisera (Kimland et al., 1989) it is possible to obtain reagents enabling specific measurement of each form of trypsinogen.

When active trypsin reaches the blood stream, it is inactivated by the major trypsin inhibitors alpha-2-macroglobulin and alpha-1-antitrypsin (AAT). AAT is a 58 kilodalton serine protease inhibitor synthesized in the liver and is one of the main protease inhibitors in blood. Whereas complexes between trypsin-1 and AAT are detectable in serum (Borgstrom and Ohlsson, 1984) the complexes with alpha -2-macroglobulin are not measurable with antibody-based assays (Ohlsson K, Acta Gastroenterol Belg 1988; 51: 3–12).

Acute pancreatitis is a severe and potentially lethal disease requiring rapid diagnosis. Determinations of amylase in serum or urine are routinely used for this purpose, but these methods are hampered by lack of specificity, which limits their clinical usefulness. Therefore, the use of other pancreatic markers, e.g. proteases and lipases have gained interest (Ogawa et al., Nippon Geka Gakkai Zassshi 1985; 86: 1241–4). Determination of trypsinogen-1 and -2 in serum (Itkonen et al., 1990) and trypsinogen-1 in urine (Lake-Bakaar et al., Lancet 1979; ii: 878–80) have been used for diagnosis of pancreatic disease.

In the present invention it has been shown that patients with pancreatic disease have strongly elevated concentrations of trypsinogen-2 complexed with alpha-1antitrypsin in serum and free trypsinogen-2 in urine. Accordingly, this discovery has proved to be very useful in the diagnosis of pancreatitis.

DETAILED DESCRIPTION OF THE INVENTION

The invention relates to an immunoassay for trypsinogen-2 wherein an amount of analyte in a sample is measured, said analyte being either trypsin-2 complexed with alpha-1-antitrypsin (trypsin -2-AAT) in serum, or trypsinogen-2 in urine.

Competitive as well as non-competitive assay methods can be employed. According to a preferred embodiment, the trypsin -2-AAT complex or free trypsinogen-2 are measured by non-competitive methods employing at least two different antibodies, where the capture antibody is bound to a solid phase.

Suitable labels are for example enzymes, radio-isotopes, fluorescent, phosforescent or luminescent markers, and colored particles that are visibly detectable. The word "label" shall also be understood to cover a binding site able to bind to the markers mentioned.

The invention further concerns a substantially purified trypsin -2-AAT complex and a substantially purified preparation of trypsinogen-2 derived from urine.

Furthermore the invention concerns methods for differentiating between pancreatitis and other pancreatic diseases on one hand and non-pancreatic disease on the other hand, either based on the determination of the concentration of trypsin -2-AAT in serum, or on the concentration of trypsinogen-2 in urine.

The invention will be illuminated by the following non-restrictive examples.

Materials Used in the Examples Presented Below

1. Monoclonal antibodies

Monoclonal antibodies were produced in mice by standard procedures. The specificity of the antibodies for trypsinogen-2 was analyzed (Itkonen et al., 1990) using trypsinogen-1 and -2 separated by ion exchange chromatography as described in the reference (Koivunen et al., 1990).

2. Reagents and Buffers

The polyclonal antiserum against AAT was obtained from Dako (Glostrup, Denmark). The assay buffer in the immunofluorometric assay (IFXA) was 50 mM Tris-HCl, pH 7.7, with 9 g/L NaCl (TBS) containing, per liter, 5 g bovine serum albumin, 0.15 g bovine globulin and 0.5 g $NaN_3$. The wash solution contained per liter, 9 g NaCl, 0.5 g $NaN_3$ and 0.2 g Tween 20™(polyoxyethylenesorbitan monolaurate). Enhancement solution was from Wallac Biochemical laboratories (Turku, Finland).

3. Samples

Serum samples were obtained from 29 patients with acute pancreatitis, 11 patients with extrahepatic biliary obstruction and 34 patients with acute abdominal disorders of extrapancreatic origin. The samples were drawn within 24 hours of admission and before initiation of therapy. The diagnosis of acute pancreatitis was based on clinical and laboratory findings (serum and urine amylase and C-reactive protein/CRP), Ranson criteria (Ranson et al., Surg Gynecol Obstet 1974; 139: 69–80). The diagnosis was confirmed by contrast computer tomography of the pancreas. The diagnosis of extrahepatic biliary obstruction and other acute abdominal disorders of extrapancreatic origin were based on regular clinical methods (clinical, laboratory, ultrasonography and radiological examinations or operative findings). Gastric and duodenal ulcers as well as oesophagitis and gastritis were diagnosed by endoscopy. Serum samples from 120 blood donors obtained from the Finnish Red Cross Blood Bank were used to establish reference values. All samples were stored at $-20°$ C. until assayed.

4. Gel Filtration

Fractionation of the trypsin -2-AAT calibrator was performed by gel filtration using a 1x30 cm column of Superdex 200™ (a copolymer of agarose and polyacrylamide) HR 10/30 (Pharmacia, Sweden) and TBS buffer for elution. Flow rate was 30 mL/h and fractions of 0.5 ml volume were collected. The tubes were prefilled with 50 µL assay buffer containing aprotinin (1.0 mg/L) in order to prevent proteolysis and nonspecific adsorption to the tubes. The elution volumes of IgG (150 kD) and albumin (69 kD) were used for a rough calibration of the column.

5. Detemination of Amylase

Amylase was measured by an enzymatic colorimetric test using an automatic analyzer (Hitachi 705E) and reagents from Boehringer Mannheim. The reference values of the method are 70–300 U/L in serum and 60–2000 U/L in urine.

EXAMPLE 1

Figure 1:
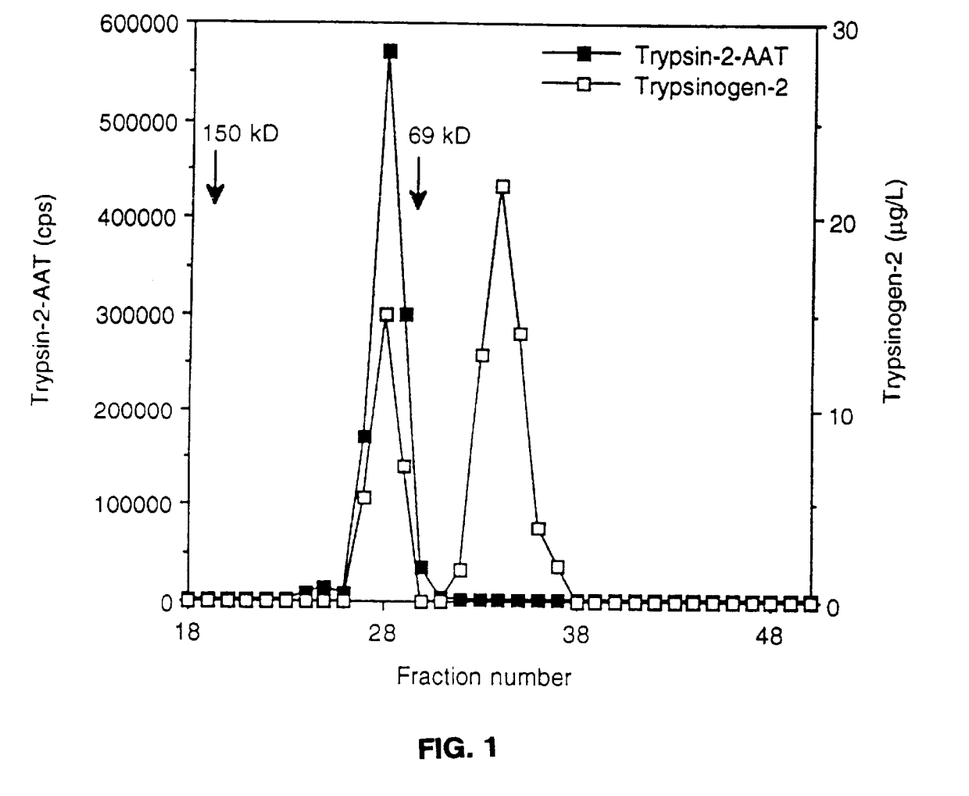
FIG. 1 presents the characterization of the trypsin-2-alpha-1-antitrypsin complex in the calibrator by gel filtration. The elution of trypsinogen-2 immunoreactivity is shown for comparison. Arrows indicate the elution positions for IgG and albumin.

Preparation of Trypsin -2-Alpha-1-Antitrypsin (Trypsin -2-AAT) for use as calibrator A calibrator for the trypsin -2-AAT complex was prepared from pure human AAT (Sigma Chemical Co., St. Louis, USA) and trypsin-2 purified as described earlier (Itkonen et al., 1990) from urine of a patient with acute pancreatitis. Trypsinogen-2 was autoactivated at +37° C. for 2 h and then incubated for 16 h at +20° C. with a seven-fold molar excess of AAT in TBS buffer. The incubation mixture was separated by gel filtration and the content of trypsinogen-2 and trypsin -2-AAT in the fractions was estimated by trypsinogen-2 IFMA (FIG. 1). Incubation with AAT reduced the trypsinogen-2 component to 6% of the content in the control incubated with aprotinin. The cross reaction in the trypsinogen-2 IFXA with trypsin -2-AAT is 3.3% (FIG. 1). On the basis of this it was calculated that 94% of trypsin-2 had complexed with AAT. This preparation was used for calibration of the trypsin -2-AAT assay.

Calibrators were prepared by diluting the complex with assay buffer to contain trypsin -2-AAT at concentrations of 0.1, 0.5, 1.0, 10, and 100 µg/L.

EXAMPLE 2

Non-Competitive Immunofluorometric Assay of Trypsinogen-2 and Trypsin -2-AAT

Trypsinogen-2 was determined with a non-competitive time-resolved immunofluorometric assay using two monoclonal antibodies (Itkonen et al., 1990). The reference range for trypsinogen-2 in serum was 18–90 µg/L (median 39 µg/L).

Figure 2:
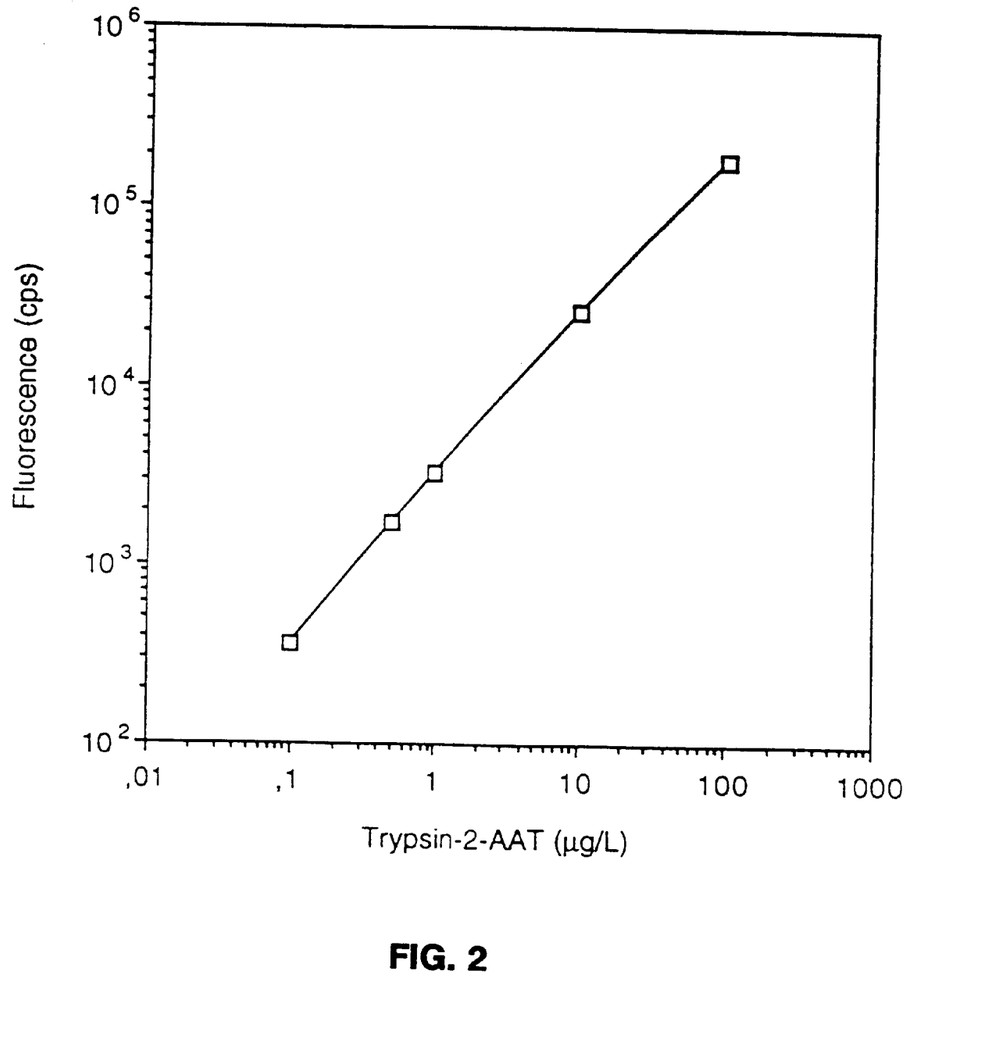
FIG. 2 presents the dose-response curve for the immunofluorometric assay of trypsin -2-alpha-1-antitrypsin complex with the calibrator used.

For assay of trypsin -2-AAT a monoclonal capture antibody to trypsin-2 (14F10) (Itkonen et al, 1990) reacting both with free trypsinogen-2 and trypsin -2-AAT complex was coated onto microtitration wells. A polyclonal rabbit antibody to AAT (Dako, Denmark) labelled with a europium chelate (Hemmilä et al, Anal Biochem 1984; 137: 335–43) was used as detector antibody. Twenty-five µL of sample and 200 µL of assay buffer were pipetted into the coated wells. After incubation for one hour the wells were emptied, washed twice with wash solution using an automatic washer (DELFIA Platewash 1296–024, Wallac, Turku, Finland). Two-hundred ng of tracer antibody in 200 µL of assay buffer was added, and after further incubation for one hour the wells were emptied and washed four times. 200 µL enhancement solution was added and after 5 min the fluorescence was measured with a 1234 DELFIA fluorometer (Wallac, Turkut Finland). The dose-response curve for the trypsin -2-AAT IFMA is shown in FIG. 2.

The detection limit of the assay was 0.05 µg/L and the standard curve was linear to 100 µg/L. The reference range determined on the basis of the 2.5 and 97.5 percentiles in sera from 120 blood donors was 2.3–12 µg/L and the median value was 4.2 µg/L.

Trypsin -2-AAT and Trypsinogen-2 in Serum in the Diagnosis of Pancreatitis

The clinical accuracy of the serum assay was estimated by determining the concentrations of trypsin -2-AAT, trypsinogen-2 and amylase in serum samples from patients with acute pancreatitis, patients with extrahepatic biliary obstruction and patients with acute abdominal disorders of extrapancreatic origin. In patients with acute pancreatitis the levels of trypsin -2-AAT and trypsinogen-2 were strongly elevated. The median concentration of trypsin -2-AAT was 59-fold that in healthy controls. That of trypsinogen-2 was 19-fold and that of amylase 5.4-fold that in healthy controls (Table 1).

TABLE 1

Median value and range of trypsin-2-AAT, trypsinogen-2 and amylase in serum from healthy controls and different patient groups (AAT abbreviation for alpha-1-antitrypsin).

|  | trypsin-2-AAT ($\mu$g/L) | | trypsinogen-2 ($\mu$g/L) | | amylase (U/L) | |
| --- | --- | --- | --- | --- | --- | --- |
|  | Median | Range | Median | Range | Median | Range |
| Healthy controls | 4.2 | 2.1–14 | 39 | 11–233 | 180 | 60–300 |
| Biliary obstruction | 6.0 | 3.8–23 | 37 | 9.6–347 | 148 | 43–403 |
| Acute abdominal disorders | 7.6 | 2.4–36 | 27 | 7.6–145 | 178 | 78–711 |
| Acute pancreatitis | 249 | 52–2170 | 750 | 75–4750 | 969 | 151–7020 |

Figure 3A:
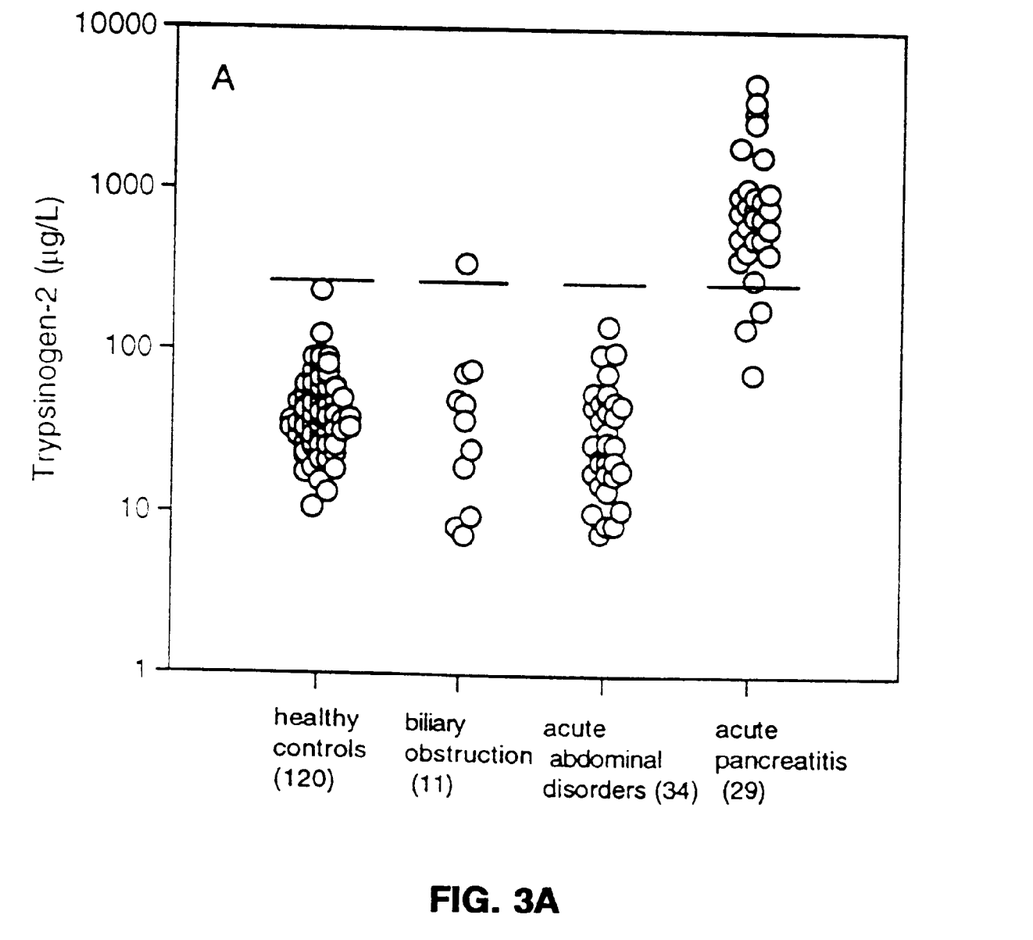
FIG. 3A presents the concentration of trypsinogen-2 in serum samples from 120 healthy controls, 11 patients with extrahepatic biliary obstruction, 34 patients with acute abdominal disorders of extrapancreatic origin and 29 patients with acute pancreatitis. The horizontal lines indicate the upper reference limits.
Figure 3B:
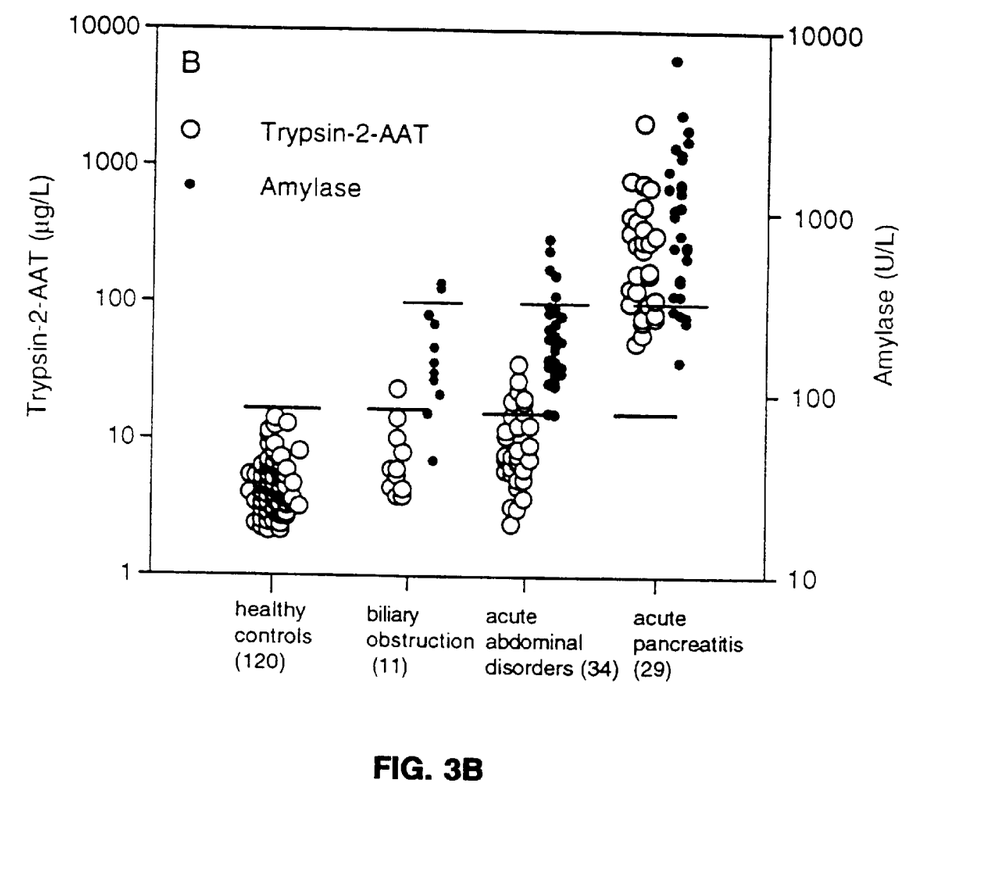
FIG. 3B presents the concentration of trypsin -2-alpha-1-antitrypsin complex and serum amylase in the same patients as in FIG. 3A.

There was no overlapping in trypsin -2-AAT values between the patients with acute pancreatitis and those with extrapancreatic disease. For trypsinogen-2 overlapping was observed in 4 patients (14%) and for amylase in 14 patients (48%) (FIGS. 3A and 3B).

Figure 4:
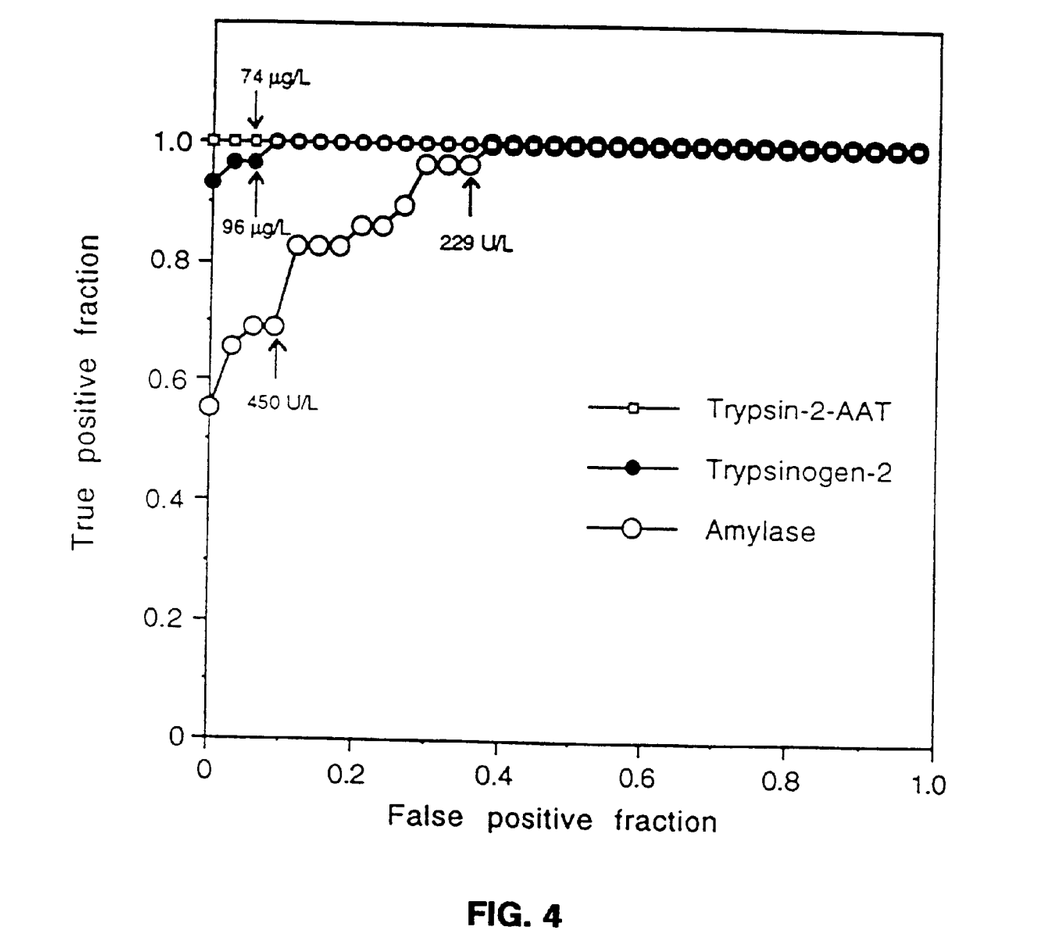
FIG. 4 presents a receiver operating characteristic (ROC) plots of trypsin -2-AAT, trypsinogen-2 and amylase in sera from 29 patients with acute pancreatitis. Patients with acute abdominal disorders of extrapancreatic origin were used as a control group. Values for some cut-off points are indicated. The figure demonstrates that trypsin -2-AAT has the best ability to discriminate between pancreatitis and nonpancreatic acute abdominal disorders.

The ability of the various analytes to differentiate between pancreatitis and non-pancreatic disease was estimated by receiver-operating characteristic (ROC) analysis. The area under the ROC curve was 1.00 for trypsin -2-AAT, 0.996 for trypsinogen-2 and 0.929 for amylase indicating that sensitivity and specificity was better for trypsin -2-AAT than for the other determinations (FIG. 4).

EXAMPLE 3
a) Purification of Trypsinogen-2 from Urine

One liter of urine containing high concentrations of trypsinogen-2 was filtered to remove insoluble constituents and the pH of the filtrate was adjusted to 7.4 with 1 mol/l NaOH. The filtrate was passed through an immunoaffinity chromatography column prepared by coupling 20 mg of the monoclonal antibody 14F10, which is specific for trypsinogen-2, to cyanogen bromide activated SEPHAROSE™ (a spherical agarose gel bead (from Pharmacia, Uppsala, Sweden). The characteristics of the antibody have been described (Itkonen et al. 1990). After washing of the column with 1 mol/l NaCl it was eluted with 0.1% trifluoroacetic acid (TFA). The eluate was further purified by reverse phase chromatography using 0.1% TFA buffer and elution with an acetonitrile gradient. The content of the fractions was monitored for protein on the basis of its absorbance at 280 nm. The fractions obtained were immediately neutralized with 1 mol/l Tris buffer. The content of trypsinogen-2 in the fractions was determined by immunoassay. The fractions containing trypsinogen-2 were concentrated. Trypsinogen-2 purified by this method was more than 95% pure as evidence by a single band in sodium dodecyl sulfate electrophoresis.

b) Trypsinogen-2 in Urine in the Diagnosis of Pancreatitis

The clinical accuracy of the urine assay for trypsinogen-2 was estimated by determining the concentrations in urine samples from 22 patients with acute pancreatitis and 46 patients with acute abdominal disorders of extrapancreatic origin. Amylase in urine was used for comparison. In patients with acute pancreatitis the levels of trypsinogen-2 were strongly elevated, the median concentrations being 4000-fold that in patients with acute abdominal disorders. The corresponding difference for amylase was only 4-fold (Table 2).

TABLE 2

Median value and range for trypsinogen-2 and amylase in urine samples of 46 patients with acute abdominal disorder of extrapancreatic origin and 22 patients with acute pancreatitis

|  | Trypsinogen-2 $\mu$g/L | | Amylase U/L | |
| --- | --- | --- | --- | --- |
|  | Median | Range | Median | Range |
| Acute abdominal disorders | 2 | 0–525 | 878 | 140–13000 |
| Acute pancreatitis | 8100 | 790–195000 | 3900 | 170–69000 |

Figure 5:
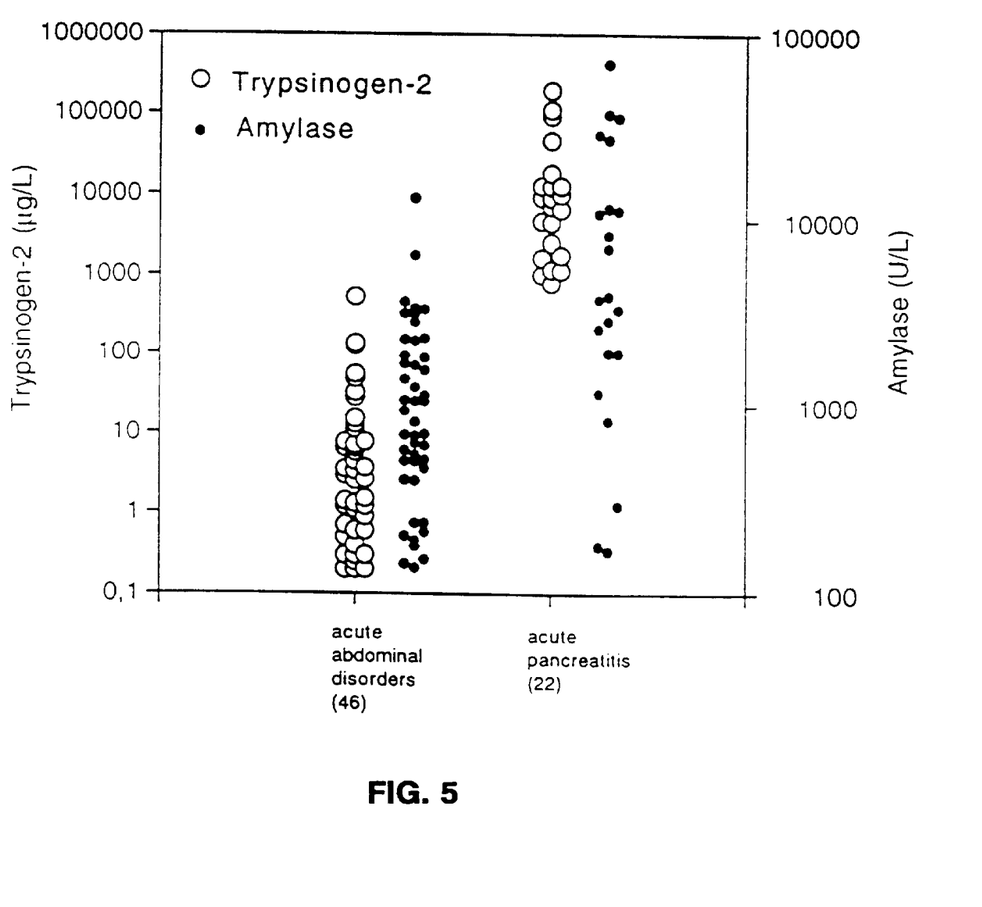
FIG. 5 presents the concentration of trypsinogen-2 and amylase in urine samples from 46 patients with acute abdominal disorders of extrapancreatic origin and from 22 patients with acute pancreatitis. The figure demonstrates that trypsinogen-2 in urine has the best diagnostic accuracy.

There was no overlapping in trypsinogen-2 values between the patients with acute pancreatitis and the control group with abdominal disorders of extrapancreatic origin. For amylase only 4 patients with pancreatics had values higher than the highest ones observed in the control group (FIG. 5).

Figure 6A:
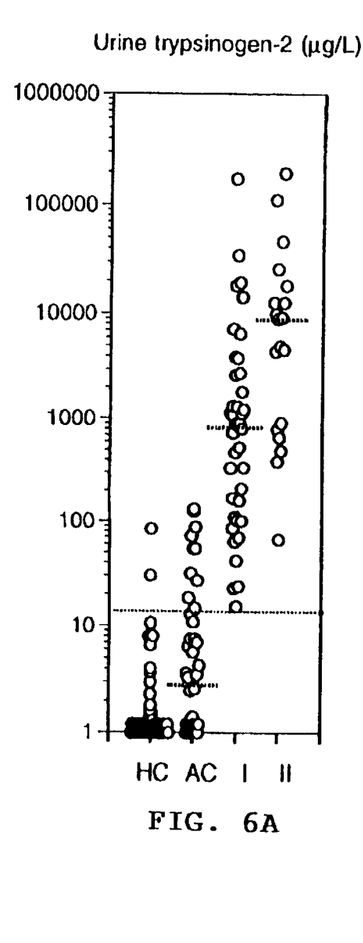
FIGS. 6A–6D show the concentrations of trypsinogen-2 and amylase in urine and serum samples from patients with mild pancreatitis (I) and severe pancreatitis (II). Patients with acute abdominal disorders of extrapancreatic origin served as controls (AC). HC=healthy controls. The dashed horizontal line indicates the upper reference limit.
Figure 6B:
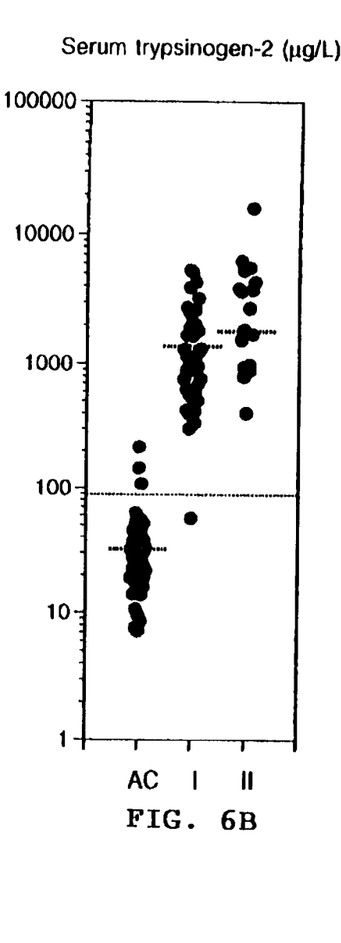

EXAMPLE 4
Urine Trypsinogen-2 as a Marker of Acute Pancreatitis Compared to Serum Trypsinogen-2 and Amylase in Serum or Urine The clinical utility of determinations of urine trypsinogen-2 in the early diagnosis and assessment of the severity of acute panceratitis (AP) was studied (FIG. 6A). As reference methods serum trypsinogen-2 (FIG. 6B), urine amylase (FIG. 6C) and serum amylase (FIG. 6D) were used. A total of 59 patients with a diagnosis of AP and 42 controls with acute upper abdominal disease of extrapancreatic origin (AC) were studied at the Helsinki University Central Hospital. The patients with AP were classified according to their clinical outcome in two groups: mild AP (group I, 40 patients) and severe AP (group II, 19 patients). Urine samples from patients without evidence of acute abdominal disease were used as healthy controls (HC). Amylase and trypsinogen were determined according to methods described before.

Figure 6C:
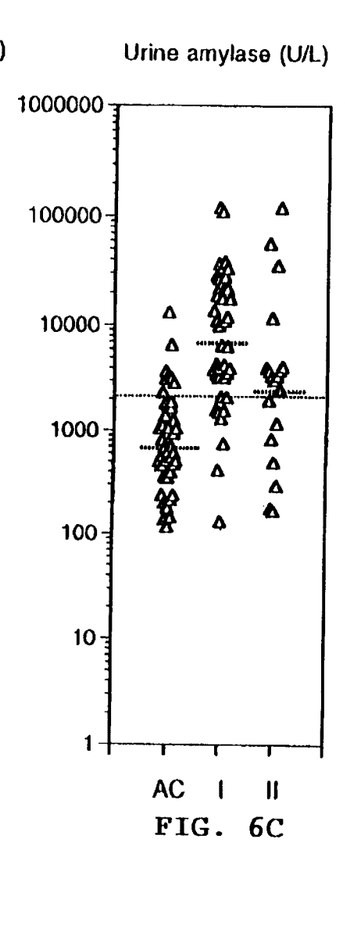
Figure 6D:
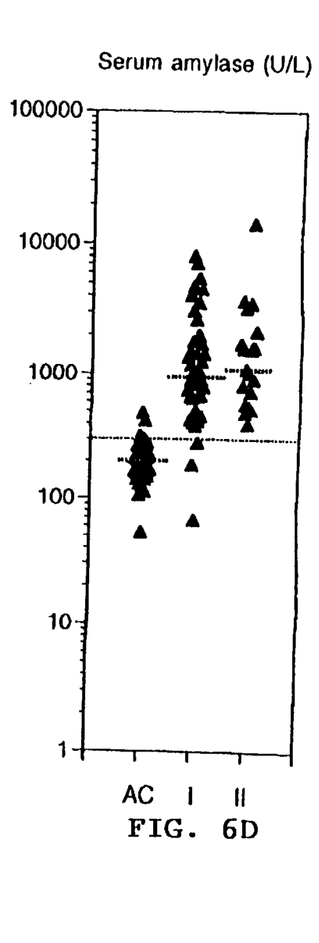

All cases of acute pancreatitis (AP) had elevated urine concentrations of trypsinogen-2 at presentation (FIG. 6A) and a concentration below the upper reference value excluded this diagnosis. In contrast, 17 (28%) of the patients with pancreatitis had a normal level of amylase in urine (FIG. 6C). The lowest trypsinogen-2 value in acute pancreatitis (15 $\mu$g/L) was 1.4-fold the upper reference limit in healthy controls. The median concentration of urine trypsinogen-2 in patients with AP was 102-fold that of the upper reference limit (FIG. 6A). For comparison, the levels of urine amylase were only 2.0-fold (FIG. 6C) and that of serum amylase 3.4-fold the upper reference limit (FIG. 6D).

Figure 7A:
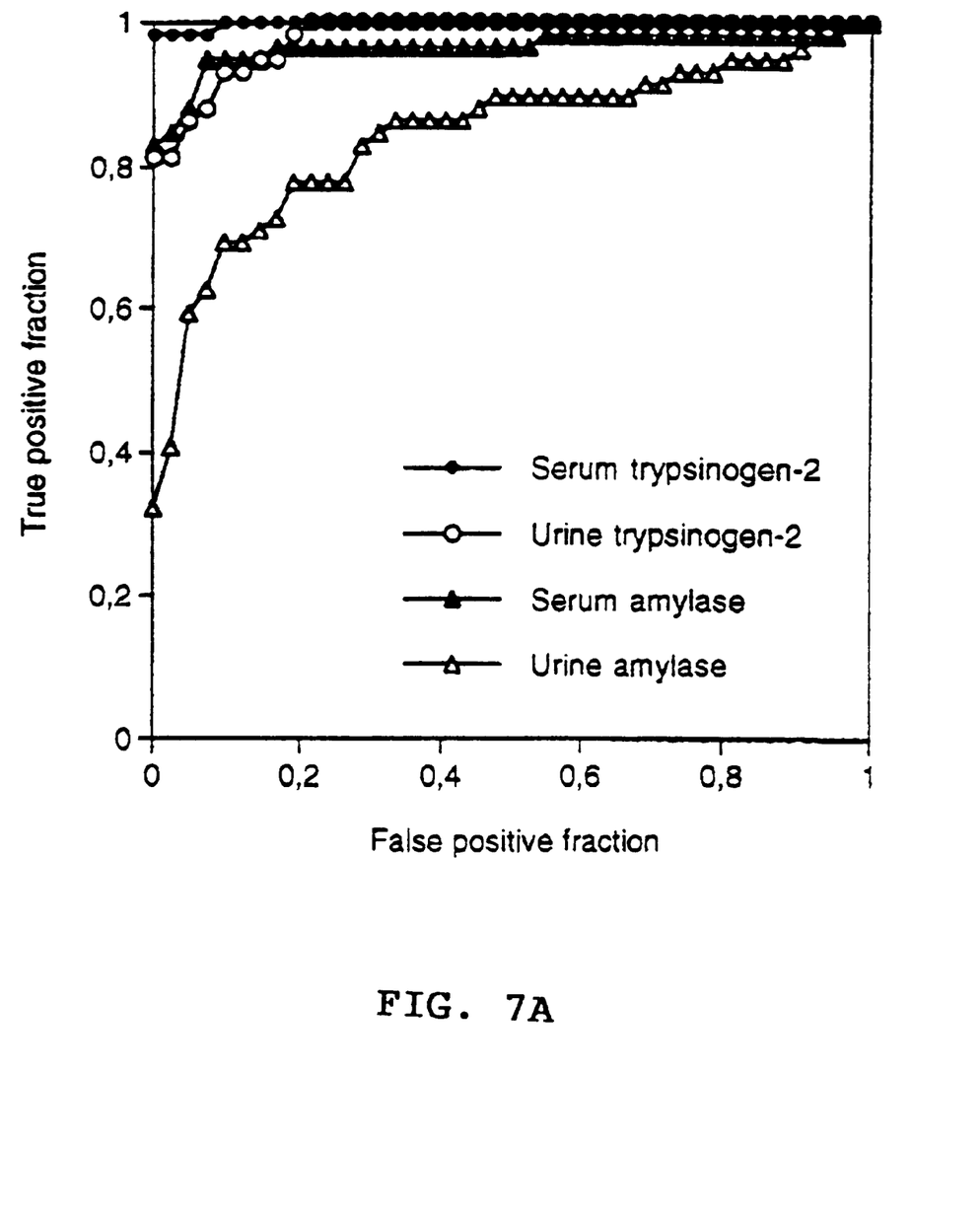
FIG. 7A–7B illustrate ROC plots showing the accuracy of the various tests in differentiating between acute pancreatitis and extrapancreatic gastrointestinal disease (FIG. 7A) and between severe and mild acute pancreatitis (FIG. 7B).

Receiver operating characteristic analysis (ROC) was used to compare patients with acute pancreatitis (AP) with controls having acute abdominal extrapancreatic disorders (AC), AUC (area under the curve) was 0.980 for trypsinogen-2 in urine and 0.842 for amylase in urine. Trypsinogen-2 in urine had as good accuracy as trypsinogen-2 in serum (AUC=0.998) and serum amylase (AUC=0.965), see FIG. 7A.

Figure 7B:
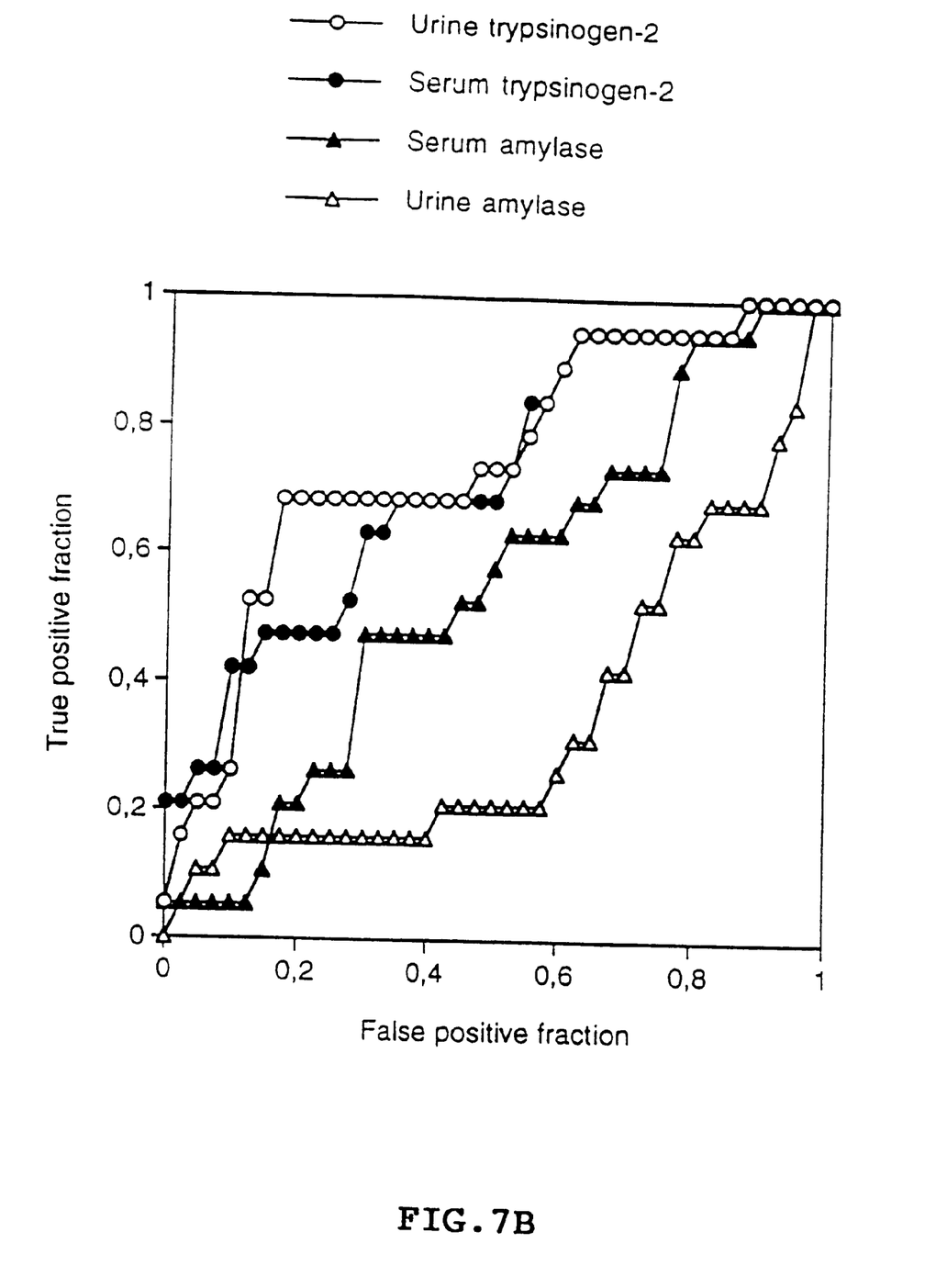

ROC-analysis showed that urine trypsinogen-2 had the highest accuracy of the markers studied in differentiating severe from mild AP (AUC=0.741, FIG. 7B) and it was slightly better than serum trypsinogen-2 in this respect. Amylase had poor ability to differentiate severe from mild AP and the levels of urine amylase were actually lower in severe than in mild disease (FIG. 6C).

These results show that trypsinogen-2 in urine is a marker with high accuracy for acute pancreatitis. All patients with acute pancreatitis have elevated values, and the number of false positive results for trypsinogen-2 in patients with other gastrointestinal diseases is lower than for urine amylase. Furthermore the level of trypsinogen-2 reflects the severity of the disease, which the amylase level does not do. Thus trypsinogen-2 is clearly superior to other urine test in the diagnosis of acute pancreatitis and is equal to the serum test for trypsinogen-2.

It is obvious from the presented data that determination of trypsin -2-AAT in serum or trypsinogen-2 in urine provides better clinical accuracy than presently used methods such as trypsinogen-2 or amylase in serum or amylase in urine.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

We claim:

1. A method for determining whether a human patient has acute pancreatitis, wherein said method comprises the steps of:
    (a) (i) measuring a concentration of trypsin-2 complexed with $\alpha_1$-antitrypsin (trypsin-2-AAT) in a serum sample from said patient by contacting said serum sample from said patient with a capture antibody specific for said trypsin-2-AAT to form an immune complex correlative of the concentration of said trypsin-2-AAT in said serum sample from said patient, and
        (ii) comparing said concentration of said trypsin-2-AAT in said serum sample from said patient with a range of concentrations of said trypsin-2-AAT in serum samples from healthy humans measured with said capture antibody, or
    (b) (i) measuring a concentration of free trypsinogen-2 in a urine sample from said patient by contacting said urine sample from said patient with a capture antibody specific for said trypsinogen-2 to form an immune complex correlative of the concentration of said free trypsinogen-2 in said urine sample from said patient, and
        (ii) comparing said concentration of said free trypsinogen-2 in said urine sample from said patient with a range of concentrations of said free trypsinogen-2 in urine samples from healthy humans measured with said capture antibody,
    wherein when (a) said concentration of said trypsin-2-AAT in said serum sample from said patient or (b) said concentration of said free trypsinogen-2 in said urine sample from said patient is greater than said respective range of concentrations, then said patient has acute pancreatitis.

2. The method according to claim 1 wherein said contacting is performed in the presence of (a) a labeled trypsin-2-AAT or (b) a labeled free trypsinogen-2 which competes with said (a) trypsin-2-AAT or (b) free trypsinogen-2 for binding to said capture antibody.

3. The method according to claim 2 wherein said labeled trypsin-2-AAT or said labeled trypsinogen-2 comprises a label selected from the group consisting of an enzyme, a radioisotope, a fluorophore, a phosphore, a luminophore, and a colored particle.

4. The method according to claim 2 wherein said labeled trypsin-2-AAT or said labeled trypsinogen-2 is indirectly labeled with an enzyme, a radioisotope, a fluorophore, a phosphore, a luminophore or a colored particle.

5. The method according to claim 1 wherein said contacting is performed in the presence of (a) a labeled detector antibody specific for said trypsin-2-AAT or (b) a labeled detector antibody specific for said free trypsinogen-2 wherein said capture antibody and said labeled detector antibody are each specific for a different second site on said trypsin-2-AAT or said free trypsinogen-2.

6. The method according to claim 5 wherein said capture antibody is bound to a solid phase prior to said contacting.

7. The method according to claim 6 wherein said trypsin-2-AAT is measured, said serum sample from said patient is sequentially contacted first with said capture antibody and then with said labeled detector antibody, and further wherein AAT not complexed with said trypsin-2 is removed before the step of contacting with said labeled detector antibody.

8. The method according to claim 7 wherein said capture antibody is specific for the trypsin-2 moiety of said trypsin-2-AAT.

9. The method according to claim 7 wherein said labeled detector antibody is specific for AAT when said AAT is complexed with said trypsin-2.

10. The method according to claim 5 wherein said capture antibody is specific for the trypsin-2 moiety of said trypsin-2-AAT.

11. The method according to claim 5 wherein said trypsin-2-AAT is measured, said serum sample from said patient is sequentially contacted first with said capture antibody and then with said labeled detector antibody, and further wherein AAT not complexed with said trypsin-2 is removed before the step of contacting with said labeled detector antibody.

12. The method according to claim 11 wherein said capture antibody is specific for the trypsin-2 moiety of said trypsin-2-AAT.

13. The method according to claim 12 wherein said labeled detector antibody is specific for AAT when said AAT is complexed with said trypsin-2.

14. The method according to claim 11 wherein said labeled detector antibody is specific for AAT when said AAT is complexed with said trypsin-2.

15. The method according to claim 1 wherein said capture antibody is bound to a solid phase prior to said contacting.

16. The method according to claim 1 wherein said capture antibody is specific for the trypsin-2 moiety of said trypsin-2-AAT.

* * * * *